United States Patent [19]

Hoshino et al.

[11] Patent Number: 5,508,025

[45] Date of Patent: Apr. 16, 1996

[54] NAPHTHALENEMETHYLENEMALONIC DIESTERS, AND UV ABSORBERS AND COSMETIC COMPOSITIONS CONTAINING THE DIESTERS

[75] Inventors: Masahide Hoshino, Kaminokawa; Mitsuru Sugiyama, Ichikai; Akira Kawamata, Utsunomiya; Hiroko Joukura, Utsunomiya; Genji Imokawa, Utsunomiya, all of Japan

[73] Assignee: Kao Corporation, Tokyo, Japan

[21] Appl. No.: 363,247

[22] Filed: Dec. 23, 1994

[30] Foreign Application Priority Data

Dec. 24, 1993 [JP] Japan .................................. 5-327597
Dec. 24, 1993 [JP] Japan .................................. 5-327598

[51] Int. Cl.$^6$ .................................................. A61K 7/42
[52] U.S. Cl. ........................... 424/59; 424/60; 514/547; 560/82
[58] Field of Search ................... 514/547; 560/82; 424/59, 60

[56] References Cited

U.S. PATENT DOCUMENTS 3,981,882  9/1976  Meyer .............................. 260/295.5 R

FOREIGN PATENT DOCUMENTS 0100651  2/1984  European Pat. Off. .
0171875  2/1986  European Pat. Off. .
0207287  1/1987  European Pat. Off. .
0350386  1/1990  European Pat. Off. .

OTHER PUBLICATIONS

Kharas G. B, Watson K. "New Copolymers of Styreue with Some Trisubstituted Ethylenes". Macromolecules 22 3871–3877 (1989).

Journal of the American Chemical Society, vol. 107, No. 25, pp. 7744–7756, Dec. 11, 1985, Howard E. Zimmerman, et al. "Rapidly Rearranging Excited States of Bichromophoric Molecules–Mechanistic and Exploratory Organic Photochemistry".

*Primary Examiner*—C. Warren Ivy
*Assistant Examiner*—Evelyn Huang
*Attorney, Agent, or Firm*—Oblon, Spivak, McClelland, Maier & Neustadt

[57] ABSTRACT

The invention relates to UV absorbers and cosmetic compositions containing a naphthalenemethylenemalonic diester represented by the following formula (1):

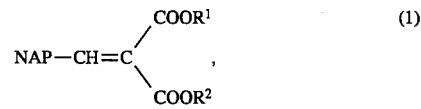

wherein NAP represents a naphthalene group which may optionally have a substituent, and $R^1$ and $R^2$ each independently represent a hydrocarbon group, an alkoxyalkyl group, or an alkoxyalkylenoxyalkyl group. The UV absorbers and the cosmetic compositions of the invention exhibit excellent ultraviolet ray absorbing action, and are stable to light.

15 Claims, No Drawings

NAPHTHALENEMETHYLENEMALONIC DIESTERS, AND UV ABSORBERS AND COSMETIC COMPOSITIONS CONTAINING THE DIESTERS

BACKGROUND OF THE INVENTION

1. Field of the Invention

The present invention relates to naphthalenemethylenemalonic diesters and to UV (ultraviolet rays) absorbers and cosmetic compositions containing the diesters.

2. Description of the Related Art

Ultraviolet rays are divided into three groups: long wavelength ultraviolet rays (UV-A) having a wavelength from 400 to 320 nm, medium wavelength ultraviolet rays (UV-B) having a wavelength from 320 to 290 nm, and short wavelength ultraviolet rays (UV-C) having a wavelength shorter than 290 nm. UV-C is absorbed in the ozone layer and therefore scarcely reaches the surface of the earth, but UV-A and UV-B are known to cause various skin disorders. For example, if a human is exposed to UV-A, his skin is immediately melanized (instant melanizing action). Subsequently, the light energy reaches the corium to affect the elastic fibers of the walls of blood vessels and connective tissues. On the other hand, excessive exposure of the skin to UV-B causes onset of erythema or bulla, and accelerates melanin formation to cause disorders such as pigmentation. Moreover, it is considered that excessive exposure of UV-A and UV-B accelerates aging of the skin, causing spots, wrinkles, and freckles to eventually trigger the onset of skin cancers. Furthermore, ultraviolet rays are known to damage hair fibers by fading their color, roughening their texture, and causing a reduction in water absorption, loss of elasticity, and changes in the keratinous structure.

As the effects of ultraviolet rays on the human skin and hair fibers have become clear, compounds capable of absorbing UV-A and UV-B (ultraviolet rays absorbers) have been developed. For example, as UV-A absorbing agents, those containing derivatives of benzophenone or benzoylmethane are known. As UV-B absorbing agents, those containing derivatives of cinnamic acid, benzophenone, p-aminobenzoic acid, or salicylic acid are known. However, none of them meets all the following requirements (a) to (e) of UV absorbers: (a) it must absorb UV-A and UV-B as much as possible, (b) it must be stable against light and heat, (c) it must neither be toxic to the skin nor irritate the skin, or it must not give other harmful effects to the skin, (d) it must have a long-lasting effect, and (e) it must have excellent compatibility with a cosmetic base. Particularly, conventional UV absorbers have insufficient stabilities against light (UV rays); it is known that they are decomposed by UV rays, or reaction takes place when they are exposed to UV rays (see, for example, Int. J. Cosmetic Science, 10, 53 (1988)). Decomposition of UV absorbers results in a shortened term of effectiveness. In addition, the effects of the decomposition products themselves or products yielded from the reaction of decomposition products and other ingredients of the composition cannot be ignored (Fragrance Journal 84, 32, (1987)). Furthermore, some regions of UV-A and UV-B cannot be absorbed by conventional UV absorbers.

The present inventors synthesized numerous compounds having various naphthalene skeletal structures, and investigated their UV ray absorbing action, stability against light, etc. As a result, they found that the naphthalenemethylenemalonic diesters represented by the formula (1) described hereinlater have excellent ultraviolet ray absorbing action and excellent stability against light, and thus are useful as ingredients of cosmetic compositions. The present invention was completed based on this finding.

SUMMARY OF THE INVENTION

Accordingly, an object of the present invention is to provide compounds which have excellent UV absorbing action over broader wavelength ranges, which meet the above requirements (a) to (e), and which especially have excellent stability against light.

Another object of the invention is to provide ultraviolet ray absorbing agents containing these compounds.

Specifically, the present invention provides ultraviolet ray absorbing agents containing the naphthalenemethylenemalonic diesters represented by the following formula (1):

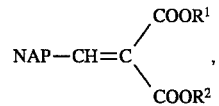

wherein NAP represents a naphthalene group which may optionally have a substituent, and $R^1$ and $R^2$ each independently represent a hydrocarbon group, an alkoxyalkyl group, or an alkoxyalkylenoxyalkyl group.

A further object of the invention is to provide cosmetic compositions containing the naphthalenemethylenemalonic diesters.

In formula (1), the compounds of the formula (2) below in which $R^1$ and $R^2$ are independently a C7–C20 hydrocarbon, an alkoxyalkyl group, or an alkoxyalkylenoxyalkyl group are novel compounds which have never been described in any publications (see Japanese Patent Application Laid-open (kokai) Nos. 49-62483 and 5-306262). Also, the compounds represented by the formula (3) below are novel compounds.

Accordingly, a still further object of the present invention is to provide the naphthalenemethylenemalonic diesters represented by formula (2):

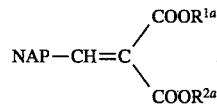

wherein NAP represents a naphthalene group which may optionally have a substituent, and $R^{1a}$ and $R^{2a}$ each independently represent a C1–C20 hydrocarbon group, a (C1–C12)alkoxy-(C1–C20)alkyl group, or a (C1–C12)alkoxy-(C1–C5)alkylenoxy-(C1–C20)alkyl group.

A yet further object of the present invention is to provide the naphthalenemethylenemalonic diesters represented by formula (3):

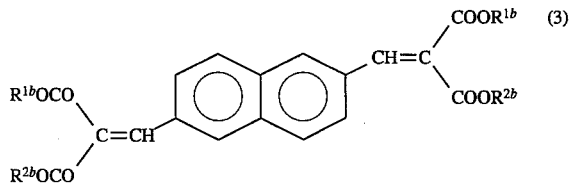

wherein $R^{1b}$ and $R^{2b}$ each independently represent a C1–C20 hydrocarbon group.

The above and other objects, features, and advantages of the present invention will become apparent from the following description.

DESCRIPTION OF PREFERRED EMBODIMENTS

The hydrocarbon groups in formula (1) which are represented by $R^1$ and $R^2$ include, but not limited to, those having 1 to 20 carbon atoms. Specific examples of the hydrocarbon groups include linear alkyl groups such as methyl, ethyl, n-propyl, n-butyl, n-pentyl, n-hexyl, n-heptyl, n-octyl, n-decyl, n-dodecyl, n-tetradecyl, n-hexadecyl, and n-octadecyl; branched alkyl groups such as isopropyl, isobutyl, t-butyl, 2,2-dimethylpropyl, 2-methylpropyl, cyclohexylmethyl, cyclohexylethyl, 2-ethylhexyl, 3,5,5-trimethylhexyl, 2-hexylundecyl, and 5,7,7-trimethyl-2-(1,3,3-trimethylbutyl)hexyl; cyclic alkyl groups such as cyclohexyl; linear alkenyl groups such as allyl, 3-butenyl, and 10-undecenyl; branched alkenyl groups such as 1-methyl-2-propenyl, 3-methyl-3-butenyl; and aralkyl groups such as benzyl. Among these, linear or branched alkyl groups are preferred, with those having 1–12 carbon atoms being particularly preferred. Moreover, it is preferred that $R^1$ and $R^2$ are the same group.

Preferable alkoxyalkyl groups represented by $R^1$ and $R^2$ are $C_{1-20}$-alkoxy-$C_{1-20}$-alkyl groups. Of $C_{1-20}$-alkoxy groups, $C_{1-12}$-alkoxy groups are particularly preferred. Examples of such alkoxy groups include methoxy, ethoxy, isopropyloxy, t-butyloxy, and 2-ethylhexyloxy. Examples of $C_{1-20}$-alkyl groups include the linear, branched or cyclic alkyl groups which have been mentioned as examples of hydrocarbon groups. Among them, $C_{1-12}$-alkyl groups are more preferred.

Examples of the alkoxyalkylenoxyalkyl groups represented by $R^1$ and $R^2$ which are preferred are $C_{1-20}$-alkoxy-$C_{1-5}$-alkylenoxy-$C_{1-20}$-alkyl groups. The $C_{1-20}$-alkoxy groups and $C_{1-20}$-alkyl groups include those mentioned as examples of the alkoxyalkyl groups. Examples of the $C_{1-5}$-alkylenoxy groups include —$CH_2O$—, —$CH_2CH_2O$—, —$CH_2CH_2CH_2O$—, $$-\underset{\underset{CH_3}{|}}{C}HCH_2O-, \text{ and } -CH_2-\underset{\underset{CH_3}{|}}{C}HO-.$$

Particularly, $C_{1-12}$-alkoxy-$C_{1-5}$-alkylenoxy-$C_{1-12}$-alkyl groups are more preferred.

Examples of the naphthalene groups which are represented by NAP in formula (1) and which may optionally have a substituent include those which have one or two substituents such as alkoxy, alkenyloxy, hydroxy, acyl, alkyl, alkenyl, $$-CH=C\genfrac{}{}{0pt}{}{COOR^1}{COOR^2},$$

(wherein $R^1$ and $R^2$ have the same meaning as defined above) may be substituted.

Among the compounds of formula (1), the following compounds represented by formula (4) are more preferred.

wherein $R^1$ and $R^2$ each independently represent a hydrocarbon group, an alkoxyalkyl group, or an alkoxyalkylenoxyalkyl group, $R^3$ represents a hydrogen atom, an alkoxy group, an alkenyloxy group, a hydroxy group, an acyl group, an alkyl group, or an alkenyl group, and $R^4$ represents a hydrogen atom, an alkoxy group, an alkenyloxy group, a hydroxy group, an acyl group, an alkyl group, an alkenyl group, or $$-CH=C\genfrac{}{}{0pt}{}{COOR^1}{COOR^2},$$

wherein $R^1$ and $R^2$ have the same meaning as defined above.

It is preferred that the alkoxy groups represented by $R^3$ and $R^4$ in formula (4) have 1 to 20 carbon atoms, with $C_{1-12}$ alkoxy groups being more preferred. Specific examples of such alkoxy groups include methoxy, ethoxy, isopropyloxy, t-butyloxy, and 2-ethylhexyloxy.

It is preferred that the alkenyloxy groups have 2 to 20 carbon atoms. Among them, $C_2$–$C_{12}$ alkenyloxy groups are more preferred. Specific examples of such alkenyloxy groups include allyloxy and 3-butenyloxy.

It is preferred that the acyl groups have 2 to 20 carbon atoms. Among them, $C_2$–$C_{12}$ acyl groups are more preferred. Specific examples of such acyl groups include acetyl, propionyl, and benzoyl.

The alkyl groups and alkenyl groups are preferably C1–C20 alkyl groups and C2–C20 alkenyl groups. Particularly, C1–C12 alkyl groups and C2–C12 alkenyl groups are more preferred. Specific examples of such alkyl groups and alkenyl groups include the groups which were mentioned in relation to $R^1$ and $R^2$.

It is particularly preferred that $R^3$ be a hydrogen atom, an alkoxy group or a hydroxy group. Also, it is particularly preferred that $R^4$ be a hydrogen atom, an alkoxy group, or a group $$-CH=C\genfrac{}{}{0pt}{}{COOR^1}{COOR^2}.$$

The group $$-CH=C\genfrac{}{}{0pt}{}{COOR^1}{COOR^2}$$

in formula (4) may be substituted at either the first or the second position of the naphthalene skeleton.

Also, among the compounds of formula (4) where $R^4$ is $$-CH=C\genfrac{}{}{0pt}{}{COOR^1}{COOR^2},$$

those represented by formula (5) are particularly preferred.

wherein $R^1$ and $R^2$ have the same meaning as defined above.

Among the compounds of formula (2), those represented by formula (6) are particularly preferred.

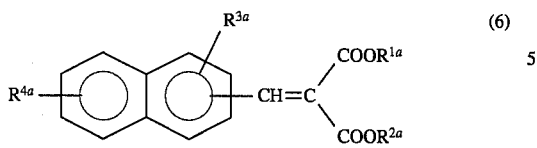

(6)

wherein $R^{3a}$ represents a hydrogen atom, a C1–C20 alkoxy group or a hydroxy group, $R^{4a}$ represents a hydrogen atom, a C1–C20 alkoxy group, and $R^{1a}$ and $R^{2a}$ have the same meaning as defined above.

The method of producing the naphthalenemethylenemalonic diesters represented by formula (1) will next be described. Naphthalenemethylenemalonic diesters (1) can be obtained by condensing (Knoevenagel condensation) a naphthylaldehyde derivative (2) and a malonic diester (3) with or without solvent and in the presence of a catalyst (see the following reaction scheme).

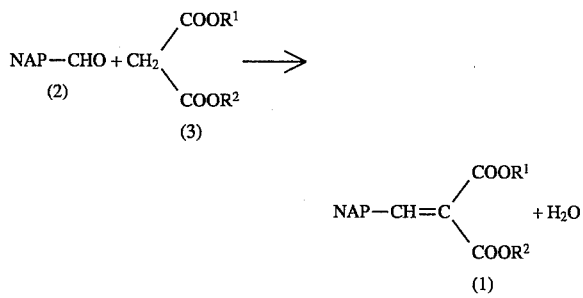

wherein NAP, $R^1$, and $R^2$ have the same meaning as defined above.

Examples of the solvent used in this reaction include benzene, toluene, xylene, tetrahydrofuran, 1,4-dioxane, and alcohols. Examples of the catalyst include amines such as piperidine and pyridine; acids such as acetic acid, benzoic acid, zinc chloride, and titanium tetrachloride; carboxylic acid salts such as sodium acetate and ammonium acetate; and acid anhydrides such as acetic anhydride. They may be used in suitable combinations. This reaction is preferably carried out with heat while removing water generated from the reaction.

In the above reaction scheme, when a formyl group is present in the NAP, two mols of malonic diester (3) is condensed to produce the compounds of formulas (5) and (6).

The UV absorbers according to the present invention can be made up by one or more naphthalenemethylenemalonic diesters of formula (1) alone. However, it is preferred that the diesters be carried by a suitable carrier. No restrictions are imposed on the carriers as long as they are inert with respect to the naphthalenemethylenemalonic diesters represented by formula (1). The carriers may take solid, liquid, emulsion, foam, or gel forms. Examples of the carriers include water; alcohols; oils and fats such as hydrocarbons, fatty acid esters, higher alcohols, and silicone oils; fine powders such as starch and talc; and agents for aerosol jetting such as low-boiling point hydrocarbons and hydrocarbon halides.

The UV absorbers according to the present invention may contain other optional UV absorbers. Examples of the optional UV absorbers include p-methylbenzylidene-D,L-camphor and sodium sulfonate salts thereof, sodium 2-phenylbenzimidazole-5-sulfonates, sodium 3,4-dimethylphenylglyoxylates, 4-phenylbenzophenone, 4-phenylbenzophenone-2'-carboxylic acid isooctyl esters, 4-methoxy cinnamic acid esters, 2-phenyl-5-methylbenzoxazoles, 4-dimethylaminobenzoic acid esters, 4-methoxy-2'-carboxydibenzoyl methanes, 4-methoxy-4'-t-butyldibenzoyl methanes, 4-isopropyldibenzoyl methanes, 1-(3,4-dimethoxyphenyl)-4,4-dimethyl-1,3-pentanediones, 2-hydroxy-4-methoxybenzophenones, and dibenzylidene camphors. Also, other ingredients such as preservatives, perfumes, colorants, surfactants, and UV diffusing agents may be incorporated in the UV absorbers of the present invention if desired.

Use of the UV absorbers of the present invention is not limited only to the application to the skin and the hair for UV ray screening purposes. It is to be noted that the UV absorbers of the invention can also be incorporated, as a UV screening agent, in various materials such as plastics which are affected by UV rays.

The cosmetic compositions according to the present invention can be prepared by incorporating the naphthalenemethylenemalonic diesters represented by formula (1) into known cosmetic bases along with various ingredients. The form of the cosmetic compositions is not particularly limited. The compositions may be formulated into various forms such as creams, lotions, solutions, oils, sprays, sticks, milky emulsions, foundations, ointments, shampoos, rinses, etc.

Examples of the known cosmetic bases include hydrocarbons such as solid or liquid paraffin, crystal oils, ceresine, ozokerite, and montan wax; oils and fats of vegetable or animal origin and waxes such as olive oil, earth wax, carnauba wax, lanolin, and whale wax; aliphatic acids and their esters such as stearic acid, palmitic acid, oleic acid, glyceryl monostearates, glyceryl distearates, glyceryl monooleates, isopropyl myristates, isopropyl stearates, and butyl stearates; silicones such as methylpolysiloxanes, methylpolycyclosiloxanes, methylphenylpolysiloxanes, silicone polyether copolymers; alcohols such as ethanol, isopropyl alcohol, cetyl alcohol, stearyl alcohol, palmityl alcohol, and hexyldodecyl alcohol; and polyhydric alcohols having moisture retention action such as glycol, glycerine and sorbitol.

Examples of the colorants include extender pigments such as mica, talc, sericite, kaolin, nylon powder, polymethylsylcesquioxane, and barium sulfate; organic pigments such as red #202, red #226, yellow #4, and aluminum lake; and UV diffusing agents such as titanium dioxide, zinc oxide, and iron oxide. When titanium dioxide or zinc oxide is used, fine powder of titanium dioxide or zinc oxide having a particle diameter not greater than 100 nm can be used. Moreover, zinc oxide flakes claimed in Japanese Patent Application Laid-open (kokai) 1-175921 can also be used. These extender pigments, organic pigments, UV diffusing agents may be those that have been surface-treated by a known method using a silicone such as methylhydrogen polysiloxane, perfruoroalkylphosphate, metallic soap, N-acylglutamic acid, silica, alumina, or silica·alumina.

As described above, the cosmetic compositions of the present invention may contain the above-mentioned known UV absorbers, W/O or O/W type emulsifiers, various silicone oils, polyether modified silicones for emulsifying silicone oils, polyether·alkyl-modified silicones, glyceryletherm-modified silicones, methylcellulose, ethylcellulose, carboxymethylcellulose, polyacrylic acid, tragacanth gum, agar, viscosity modifiers such as gelatin, perfumes, preservatives:, humectants, emulsion stabilizers, various medicinal components, and physiologically acceptable colorants.

The proportion of the naphthalenemethylenemalonic diesters of formula (1) in cosmetic compositions varies depending on the kinds of the cosmetics. A proportion of 0.1 to 20% by weight is generally preferred, and 0.5 to 10% by weight is particularly preferred.

EXAMPLES

The present invention will next be described by way of examples, which should not be construed as limiting the invention.

Example 1

Diethyl 2-naphthalenemethylene malonate represented by the following formula was prepared in a manner described below.

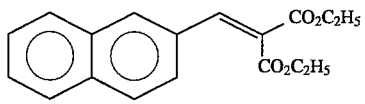

2-Naphthaldehyde (4.68 g, 0.030 mol) was placed in a two-neck flask (capacity: 300 ml), and was dissolved with benzene (150 ml). Subsequently, diethyl malonate (5.29 g, 0.033 mol), piperidine (0.30 ml, 0.003 mol), and acetic acid (0.10 ml, 0.0018 mol) were added and the resulting mixture was refluxed with heat for 36 hours while stirring and azeotropically dehydrating the generated water using a Dean Stark dehydrating apparatus. After cooled, the reaction was washed with water three times. The organic phase was dried over anhydrous sodium sulfate, after which the solvent was distilled off to obtain a yellow oily material. The oily material was purified by silica gel column chromatography using hexane - ethyl acetate (50:1 - 20:1) as a developer, yielding 8.61 g (96%) of the target compound as a colorless oil.

IR $\nu$ neat, cm$^{-1}$) : 2990, 1740, 1625, 1600, 1505, 1470, 1450, 1370, 1250, 1220, 1170, 1090, 1060, 895, 860, 745

$^1$H-NMR (CDCl$_3$, $\delta$ ppm) : 1.30 (3H, t, J=7.1 Hz), 1.35 (3H, t, J=7.1 Hz), 4.33 (2H, q, J=7.1 Hz), 4.37 (2H, q, J=7.1 Hz) , 7.40–7.60 (3H, m), 7.70–7.95 (3H, m), 7.89 (1H, s), 7.96 (1 H, br, s)

Example 2

Di(2-ethylhexyl) 2-naphthalenemethylene malonate represented by the following formula was prepared in a manner described below.

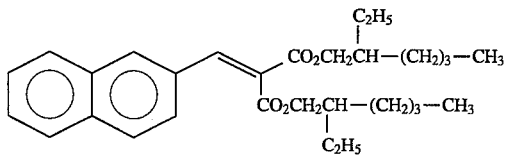

The procedure described in Example 1 was repeated using 2-naphthaldehyde (3.12 g, 0.020 mol), di(2-ethylhexyl) malonate (6.57 g, 0.020 mol), piperidine (0.20 ml, 0.002 mol), acetic acid (0.07 ml, 0.0012 mol), and benzene (100 ml). As a result, 7.75 g (yield: 83%) of the target compound was obtained as a colorless oil.

IR ($\nu$ neat, cm$^{-1}$) : 2970, 1740, 1630, 1600, 1465, 1380, 1345, 1240, 1175, 1125, 1065, 950, 860, 815, 745

$^1$H-NMR (CDCl$_3$, $\delta$ ppm): 0.79 (3H, t, J=7.3 Hz), 0.80 (3H, t, J=7.3 Hz), 0.91 (3H, t, J=7.3 Hz), 0.92 (3H, t, J=7.3 Hz), 1.10–1.50 (16H, m), 1.50–1.70 (2H, m), 4.18 (2H, d, J=5.6 Hz), 4.19 (2H, d, J=5.6 Hz), 7.45–7.60 (3H, m), 7.75–7.95 (3H, m), 7.89 (1H, s), 7.95 (1H, br, s)

Example 3

Di[2-(2-methoxyethoxy)ethyl] 2-naphthalenemethylene malonate represented by the following formula was prepared in a manner described below.

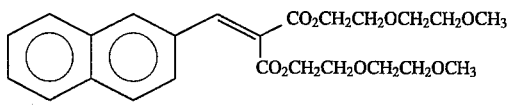

The procedure described in Example 1 was repeated using 2-naphthaldehyde (3.12 g, 0.020 mol), di[2-(2-methoxyethoxy)ethyl] malonate (6.17 g, 0.020 mol), piperidine (0.40 ml, 0.004 mol), acetic acid (0.14 ml, 0.0024 mol), and benzene (150 ml). As a result, 6.41 g (yield: 72%) of the target compound was obtained as a colorless oil.

IR ($\nu$ neat, cm$^{-1}$) : 2890, 1735, 1625, 1600, 1455, 1400, 1345, 1245, 1220, 1175, 1070, 935, 860, 820, 745

$^1$H-NMR (CDCl$_3$, $\delta$ ppm) : 3.28 (3H, s), 3.35–3.40 (2H, m), 3.40 (3H, s), 3.45–3.65 (4H, m), 3.65–3.85 (6H, m) , 4.44 (2H, t, J=5.1 Hz), 7.45–7.60 (3H, m), 7.75–7.90 (3H, m), 7.94 (1H, s), 7.97 (1H, br, s)

Example 4

Di(2-ethylhexyl) 6-methoxy-2-naphthalenemethylene malonate represented by the following formula was prepared in a manner described below.

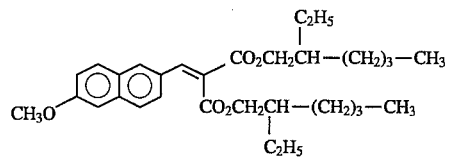

The procedure described in Example 1 was repeated using 6-methoxy-2-naphthaldehyde (3.73 g, 0.020 mol), di(2-ethylhexyl) malonate (6.57 g, 0.020 mol), piperidine (0.40 ml, 0.004 mol), acetic acid (0.14 ml, 0.0024 mol), and benzene (120 ml). As a result, 8.13 g (yield: 85%) of the target compound was obtained as a pale yellow oil.

IR ($\nu$ neat, cm$^{-1}$) : 2935, 1730, 1620, 1505, 1485, 1395, 1340, 1255, 1230, 1195, 1065, 1030, 940, 850, 810, 765

$^1$H-NMR (CDCl$_3$, $\delta$ ppm) : 0.80 (3H, t, J=7.3 Hz), 0.82 (3H, t, J=7.3 Hz), 0.91 (3H, t, J=7.3 Hz), 0.92 (3H, t, J=7.3 Hz), 1.05–1.50 (16H, m), 1.50–1.75 (2H, m), 3.93 (3H, s), 4.18 (2H, d, J=5.7 Hz), 4.19 (2H, d, J=5.7 Hz), 7.05–7.25 (2H, m), 7.48 (1H, dd, J=8.6, 1.7 Hz), 7.65–7.80 (2H, m), 7.85 (1H, s), 7.88 (1H, br, s)

Example 5

Diethyl 1-naphthalenemethylene malonate represented by the following formula was prepared in a manner described below.

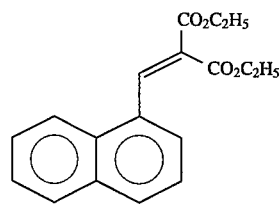

The procedure described in Example 1 was repeated using 1-naphthaldehyde (4.68 g, 0.0030 mol), diethyl malonate (5.29 g, 0.0033 mol), piperidine (0.30 ml, 0.003 mol), acetic acid (0.10 ml, 0.0018 mol), and benzene (150 ml). As a result, 8.75 g (yield: 98%) of the target compound was obtained as a pale yellow oil.

IR ($\nu$ neat, $cm^{-1}$) : 3065, 1730, 1635, 1510, 1465, 1450, 1395, 1375, 1340, 1270, 1165, 1060, 1015, 860, 800

$^1$H-NMR (CDCl$_3$, $\delta$ ppm): 1.06 (3H, t, J=7.1 Hz), 1.38 (3H, t, J=1 Hz), 4.16 (2H, q, J=7.1 Hz), 4.37 (2H, q, J=7.1 Hz), 7.35–7.65 (4H, m), 7.80–7.95 (2H, m), 7.95–8.05 (1H, m), 8.47 (1H, s)

Example 6

2,6-Naphthalenebis(diethyl methylene malonate) represented by the following formula was prepared in a manner described below.

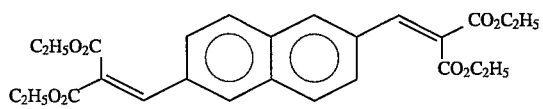

2,6-Naphthalene dialdehyde (350.0 mg, 1.90 mmol) was placed in a two-neck flask (capacity: 300 ml), and was dissolved with benzene (170 ml). Subsequently, diethyl malonate (913.0 mg, 5.70 mmol), piperidine (47 μl, 0.48 mmol), and acetic acid (16 μl, 0.29 mmol) were added, and the resulting mixture was refluxed with heat for 40 hours while stirring and azeotropically dehydrating the generated water using a Dean Stark dehydrating apparatus. After cooled, the reaction was washed with water three times. The organic phase was dried over anhydrous sodium sulfate, after which the solvent was distilled off to obtain yellow crystals. The crystals were recrystallized using ethyl acetate, yielding 533.8 mg (60%) of the target compound as pale yellow crystals.

melting point: 133.0° C.

IR ($\nu$ Kbr, $cm^{-1}$) : 1730, 1720, 1630, 1400, 1385, 1335, 1260, 1215, 1165, 1140, 1065, 1025

$^1$H-NMR (CDCl$_3$, $\delta$ ppm): 1.30 (6H, t, J=7.1 Hz), 1.36 (6H, t, J=7.1 Hz), 4.32 (4H, q, J=7.1 Hz), 4.37 (4H, q, J=7.1 Hz), 7.55 (2H, dd, J =8.5, 1.3 Hz), 7.87 (2H, d, J=8.5 Hz), 7.88 (2H, s), 7.94 (2H, br, s)

Example 7

2,6-Naphthalenebis [di(2-ethylhexyl) methylene malonate] represented by the following formula was prepared in a manner described below.

2,6-Naphthalene dialdehyde (511.0 mg, 2.77 mmol) was placed in a two-neck flask (capacity: 200 ml), and was dissolved with benzene (110 ml). Subsequently, di(2-ethylhexyl) malonate (2.00 g, 6.10 mmol), piperidine (0.11 ml, 1.11 mmol), and acetic acid (38 μl, 0.66 mmol) were added, and the resulting mixture was refluxed with heat for 76 hours while stirring and azeotropically dehydrating the generated water using a Dean Stark dehydrating apparatus. After cooled, the reaction was washed with water three times. The organic phase was dried over anhydrous sodium sulfate, after which the solvent was distilled off to obtain a brown oily material. The oily material was purified by silica gel column chromatography using hexane - ethyl acetate (50:1 - 20:1) as a developer, yielding 949.3 mg (34%) of the target compound as a pale yellow oil.

IR ($\nu$ neat, $cm^{-1}$) : 3565, 2935, 1725, 1630, 1465, 1380, 1340, 1255, 1230, 1135, 1065, 945, 815, 765

$^1$H-NMR (CDCl$_3$, $\delta$ ppm) : 0.80 (12H, t, J=7.2 Hz), 0.85–1.05 (12H, m), 1.05–1.50 (32H, m), 1.50–1.80 (4H, m), 4.10–4.30 (8H, m), 7.54 (2H, dd, J=1.1, 8.6 Hz), 7.81 (2H, d, J=8.6), 7.86 (2H, s), 7.92 (2H, br, s)

Test Example 1

The naphthalenemethylenemalonic diesters obtained in Examples 1 through 7 were used as UV absorbers, and their ultraviolet ray absorbing capability (absorption) was investigated. For comparison, known UV absorbers, 2-hydroxy-4-methoxybenzophenone (Comparative Example 1) and 2-ethylhexyl 4-methoxycinnamate (Comparative Example 2) were also tested. The results are shown in Table 1.

Method

Each UV absorber was dissolved in ethanol (99.5%, special grade) to prepare a solution having a concentration of $2.5\times10^{-5}$ mol/l. The solution was placed in a quartz cell (1×1 cm), after which its absorption was measured with a spectrophotometer of an automatic recording type (model U-3410, by Hitachi).

TABLE 1

| Wave-length (nm) | Example Nos. | | | | | | | Comparative Example Nos. | |
|---|---|---|---|---|---|---|---|---|---|
| | 1 | 2 | 3 | 4 | 5 | 6 | 7 | 1 | 2 |
| 290 | 0.34 | 0.30 | 0.31 | 0.20 | 0.13 | 0.26 | 0.26 | 0.40 | 0.54 |
| 300 | 0.51 | 0.45 | 0.47 | 0.20 | 0.19 | 0.32 | 0.30 | 0.28 | 0.60 |
| 310 | 0.59 | 0.53 | 0.57 | 0.34 | 0.24 | 0.54 | 0.49 | 0.24 | 0.64 |

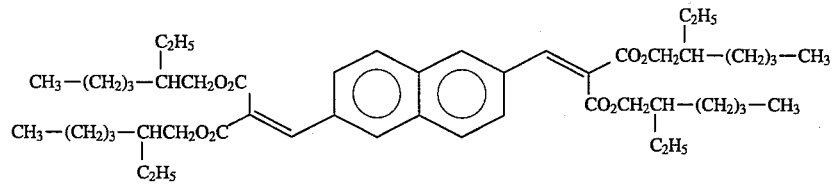

TABLE 1-continued

| Wave-length (nm) | Example Nos. | | | | | | | Comparative Example Nos. | |
|---|---|---|---|---|---|---|---|---|---|
| | 1 | 2 | 3 | 4 | 5 | 6 | 7 | 1 | 2 |
| 320 | 0.44 | 0.41 | 0.45 | 0.49 | 0.26 | 0.83 | 0.75 | 0.25 | 0.52 |
| 330 | 0.20 | 0.20 | 0.22 | 0.59 | 0.24 | 1.02 | 0.93 | 0.25 | 0.27 |
| 340 | 0.13 | 0.12 | 0.13 | 0.56 | 0.19 | 1.02 | 0.94 | 0.21 | 0.08 |
| 350 | 0.09 | 0.09 | 0.09 | 0.42 | 0.12 | 0.68 | 0.65 | 0.13 | 0.02 |
| 360 | 0.07 | 0.07 | 0.07 | 0.32 | 0.06 | 0.43 | 0.42 | 0.06 | 0.01 |
| 370 | 0.02 | 0.02 | 0.02 | 0.17 | 0.02 | 0.29 | 0.29 | 0.03 | 0.00 |
| 380 | 0.00 | 0.01 | 0.00 | 0.06 | 0.00 | 0.23 | 0.22 | 0.01 | 0.00 |
| 390 | 0.00 | 0.00 | 0.00 | 0.02 | 0.00 | 0.08 | 0.09 | 0.00 | 0.00 |
| 400 | 0.00 | 0.00 | 0.00 | 0.00 | 0.00 | 0.01 | 0.02 | 0.00 | 0.00 |

As is apparent from Table 1, the UV absorbers of the present compounds exhibited excellent UV absorption effects which are comparable to or higher than the effects of the compounds of Comparative Examples 1 or 2.

Test Example 2

The naphthalenemethylenemalonic diesters obtained in Examples 1, 2, 4, 5, 6, and 7 were used as UV absorbers, and their stabilities against light were examined by the method described below. For comparison, known UV absorbers, 2-ethylhexyl 4-methoxycinnamate (Comparative Example 2) and 2-ethylhexyl 4-dimethylaminobenzoate (Comparative Example 3) were also tested. The results are shown in Table 2.

Method

Each UV absorber was dissolved in ethanol (99.5%, special grade) to prepare a solution having a concentration of $1.0 \times 10^{-4}$ mol/l. The solution was placed in a quartz cell (1×1 cm), after which its absorption was measured with a spectrophotometer of an automatic recording type (model U-3410, by Hitachi). Next, each solution in quartz cell was irradiated with light having a wavelength and intensity similar to the sunlight in the summer time using a xenon light resistance tester (model type: SUNTEST CPS, by Heraeus) for 2 or 6 hours. Subsequent to the exposure to the light, absorption of the solution was measured again in a manner similar to that in the first measurement. From the absorption data obtained in the first and second measurements, the residual UV ray absorption effect was calculated to evaluate the stability against light. The residual effect is expressed by the percentage obtained by dividing the absorption at $\lambda_{max}$ after undergoing light exposure by the absorption at $\lambda_{max}$ before undergoing light exposure.

TABLE 2

| | Residual UV absorbing effect (%) | |
|---|---|---|
| Tested compounds | After 2 hours from irradiation of light | After 6 hours from irradiation of light |
| Compound of Example 1 | 98 | 95 |
| Compound of Example 2 | 99 | 97 |
| Compound of Example 4 | 97 | 93 |
| Compound of Example 5 | 99 | 98 |
| Compound of Example 6 | 97 | 92 |
| Compound of Example 7 | 97 | 93 |
| Compound of Comparative Example 2 | 70 | 69 |
| Compound of Comparative Example 3 | 83 | 55 |

As is apparent from Table 2, the UV absorbers of the present invention maintained notably higher UV absorbing capability after irradiation of 2 or 6 hours than the UV absorbers of the comparative examples. Moreover, the UV absorbing effects of the present compounds dropped only slightly after passage of time.

Example 8

A powder foundation of the following formulation was prepared by a routine method.

| Formulation: | (% by weight) |
|---|---|
| Mica | balance |
| Talc | 20 |
| Titanium dioxide | 10 |
| Red iron oxide | 1 |
| Iron (III) oxide | 2 |
| Iron (II) oxide | 1 |
| Liquid paraffin | 10 |
| Beeswax | 2 |
| Preservative | suitable amount |
| Compound of Example 1 or Example 6 | 5 |
| Perfume | suitable amount |
| total: | 100 |

Example 9

A creamy foundation of the following formulation was prepared by a routine method.

| Formulation: | (% by weight) |
|---|---|
| Stearic acid | 5 |
| Oleophilic glyceryl monostearate | 3 |
| Cetostearyl alcohol | 1 |
| Propylene glycol monolaurate | 3 |
| Squalane | 7 |
| Olive oil | 8 |
| Purified water | balance |
| Preservative | suitable amount |
| Triethanolamine | 1.2 |
| Sorbitol | 3 |
| Titanium dioxide | 10 |
| Talc | 5 |
| Coloring pigment | suitable amount |
| Compound of Example 2 or Example 7 | 7 |
| Perfume | suitable amount |
| total: | 100 |

Example 10

An oil-base foundation of the following formulation was prepared by a routine method.

| Formulation: | (% by weight) |
|---|---|
| Compound of Example 5 | 5 |
| Talc | balance |
| Kaolin | 12 |
| Titanium dioxide | 13 |
| Red iron oxide | 1.5 |
| Iron (III) oxide | 20 |
| Iron (II) oxide | 0.5 |
| Liquid paraffin | 15 |
| Isopropyl palmitate | 10 |
| Lanolin alcohol | 3 |
| Microcrystalline wax | 7 |
| Ozokerite | 8 |
| Preservative | suitable amount |
| Perfume | suitable amount |
| total: | 100 |

Example 11

An O/W-type cream of the following formulation was prepared by a routine method.

| Formulation: | (% by weight) |
|---|---|
| Beeswax | 6 |
| Cetyl alcohol | 5 |
| Hydrogenated lanolin | 7 |
| Squalane | 33 |
| Aliphatic glycerol | 3.5 |
| Oleophilic glycerol monostearate | 2 |
| Polyoxyethylene (EO 20) sorbitan monolaurate | 2 |
| Compound of the invention: Diallyl 4-methoxy-1-naphthalenemethylene malonate | 6 |
| Perfume | trace amount |
| Preservative | suitable amount |
| Antioxidant | suitable amount |
| Purified water | balance |
| total: | 100 |

Example 12

A W/O-type cream of the following formulation was prepared by a routine method.

| Formulation: | (% by weight) |
|---|---|
| Compound of Example 4 | 5 |
| 2-Ethylhexyl 4-methoxycinnamate | 3 |
| Silicone-treated titanium dioxide | 0.5 |
| Dimethylpolysiloxane · methyl (polyoxyethylene) siloxane copolymer | 3 |
| Methylpolysiloxane | 10 |
| Methylpolycyclopolysiloxane | 10 |
| Squalane | 5 |
| Magnesium sulfate | 0.7 |
| Glycerol | 7 |
| Perfume | trace amount |
| Preservative | suitable amount |
| Antioxidant | suitable amount |
| Purified water | balance |
| total: | 100 |

Example 13

A W/O-type cream of the following formulation was prepared by a routine method.

| Formulation: | (% by weight) |
|---|---|
| Compound of Example 2 or Example 7 | 4 |
| Silicone-treated zinc oxide flakes | 2 |
| 2-Ethylhexyl 4-methoxycinnamate | 4 |
| Dimethylpolysiloxane · methyl (polyoxyethylene) siloxane copolymer | 3 |
| Methylpolysiloxane | 10 |
| Methylpolycyclopolysiloxane | 10 |
| Squalane | 4 |
| Magnesium sulfate | 0.5 |
| Glycerol | 7 |
| Perfume | trace amount |
| Preservative | suitable amount |
| Antioxidant | suitable amount |
| Purified water | balance |
| total: | 100 |

Example 14

A W/O-type cream of the following formulation was prepared by a routine method.

| Formulation: | (% by weight) |
|---|---|
| Compound of the invention: Di(3,3,5-trimethyl-hexyl) 2-naphthalenemethylene malonate | 4 |
| Silicone-treated zinc oxide flakes | 2 |
| 2-Ethylhexyl 4-methoxycinnamate | 4 |
| Dimethylpolysiloxane · methyl (polyoxyethylene) siloxane copolymer | 3 |
| Methylpolysiloxane | 10 |
| Methylpolycyclopolysiloxane | 10 |
| Squalane | 4 |
| Magnesium sulfate | 0.5 |
| Glycerol | 7 |
| Perfume | trace amount |
| Preservative | suitable amount |
| Antioxidant | suitable amount |
| Purified water | balance |
| total: | 100 |

Examples 15 and 16

Using di(2-hexylundecyl) 2-naphthalenemethylene malonate and di(3-methyl-3-butenyl) 2-naphthalenemethylene malonate, each in amount of 4% by weight, the procedure of Example 14 was repeated to prepare W/O-type creams.

Example 17

An O/W-type milky emulsion of the following formulation was prepared by a routine method.

| Formulation: | (% by weight) |
|---|---|
| Compound of Example 3 or Example 7 | 4 |
| Silicone-treated titanium dioxide | 1 |
| 2-Ethylhexyl 4-methoxycinnamate | 4 |
| Sorbitan sesquioleate | 0.8 |
| Polyoxyethylene (EO 20) oleylether | 1.2 |
| Squalane | 5 |
| Vaseline | 2 |
| Beeswax | 0.5 |
| Silicone-treated talc | 5 |
| Propylene glycol | 5 |
| Ethanol | 5 |

| Formulation: | (% by weight) |
| --- | --- |
| Carboxyvinyl polymer (10% aqueous solution) | 20 |
| Potassium hydroxide | 0.1 |
| Purified water | balance |
| total: | 100 |

Example 18

An O/W-type milky emulsion of the following formulation was prepared by a routine method.

| Formulation: | (% by weight) |
| --- | --- |
| Compound of the invention: Di(n-octadecyl)2-hydroxy-1-naphthalenemethylene malonate | 5 |
| 2-Ethylhexyl 4-methoxycinnamate | 2 |
| Silicone-treated titanium dioxide | 1 |
| Oleophilic glyceryl monooleate | 2 |
| Polyoxyethylene (EO 20) sorbitan monolaurate | 1 |
| Squalane | 10 |
| Silicone-treated talc | 5 |
| Glycerol | 5 |
| Preservative | suitable amount |
| Perfume | suitable amount |
| Antioxidant | suitable amount |
| Purified water | balance |
| total: | 100 |

Example 19

An oil-base foundation of the following formulation was prepared by a routine method.

| Formulation: | (% by weight) |
| --- | --- |
| Compound of the invention: 2,6-Naphthalenebis[di(3-methyl-3-butenyl)methylene malonate] | 5 |
| Talc | suitable amount |
| Kaolin | 12 |
| Titanium dioxide | 13 |
| Red iron oxide | 1.5 |
| Iron (III) oxide | 20 |
| Iron (II) oxide | 0.5 |
| Liquid paraffin | 15 |
| Isopropyl palmitate | 10 |
| Lanolin alcohol | 3 |
| Microcrystalline wax | 7 |
| Ozokerite | 8 |
| Preservative | suitable amount |
| Perfume | suitable amount |
| total: | 100 |

Example 20

An O/W-type cream of the following formulation was prepared by a routine method.

| Formulation: | (% by weight) |
| --- | --- |
| Beeswax | 6 |
| Cetyl alcohol | 5 |
| Hydrogenated lanolin | 7 |
| Squalane | 33 |
| Aliphatic glycerol | 3.5 |
| Oleophilic glycerol monostearate | 2 |

| Formulation: | (% by weight) |
| --- | --- |
| Polyoxyethylene (EO 20) sorbitan monolaurate | 2 |
| Compound of the invention: 2,6-Naphthalenebis [di(3,5,5-trimethylhexyl) methylene malonate] | 6 |
| Perfume | trace amount |
| Preservative | suitable amount |
| Antioxidant | suitable amount |
| Purified water | balance |
| total: | 100 |

Example 21

A W/O-type cream of the following formulation was prepared by a routine method.

| Formulation: | (% by weight) |
| --- | --- |
| Compound of the invention: 2,6-Naphthalenebis [di(2-hexyldecyl) methylene malonate] | 5 |
| 2-Ethylhexyl 4-methoxycinnamate | 3 |
| Silicone-treated titanium dioxide | 0.5 |
| Dimethylpolysiloxane · methyl (polyoxyethylene) siloxane copolymer | 3 |
| Methylpolysiloxane | 10 |
| Methylpolycyclopolysiloxane | 10 |
| Squalane | 5 |
| Magnesium sulfate | 0.7 |
| Glycerol | 7 |
| Perfume | trace amount |
| Preservative | suitable amount |
| Antioxidant | suitable amount |
| Purified water | balance |
| total: | 100 |

Example 22

An O/W-type cream of the following formulation was prepared by a routine method.

| Formulation: | (% by weight) |
| --- | --- |
| Compound of the invention: 2,6-Naphthalenebis (diallyl methylene malonate) | 5 |
| 2-Ethylhexyl 4-methoxycinnamate | 2 |
| Silicone-treated titanium dioxide | 1 |
| Oleophilic glyceryl monooleate | 2 |
| Polyoxyethylene (EO 20) sorbitan monolaurate | 1 |
| Squalane | 10 |
| Silicone-treated talc | 5 |
| Glycerol | 5 |
| Preservative | suitable amount |
| Perfume | suitable amount |
| Antioxidant | suitable amount |
| Purified water | balance |
| total: | 100 |

The naphthalenemethylenemalonic diesters of the present invention have excellent ultraviolet ray absorbing effect over the ranges covering almost all UV-B and UV-A wavelengths. In addition, they are stable against light, and practically, they are not decomposed by sunlight in a dose which humans receive in their daily lives. Therefore, the skin is scarcely affected by decomposition products of the compounds. Moreover, they are free from the problems of toxicity and

What is claimed is:

1. An ultraviolet ray absorber comprising a naphthalenemethylenemalonic diester represented by the following formula (1):

$$NAP-CH=C\begin{matrix}COOR^1\\COOR^2\end{matrix} \quad (1)$$

wherein NAP represents a naphthalene group which may optionally have a substituent, and $R^1$ and $R^2$ each independently represent an alkoxyalkyl group, or an alkoxyalkylenoxyalkyl group.

2. The ultraviolet ray absorber according to claim 1, comprising a naphthalenemethylenemalonic diester represented by the following formula (4):

$$R^4-\text{[naphthalene with }R^3\text{]}-CH=C\begin{matrix}COOR^1\\COOR^2\end{matrix} \quad (4)$$

wherein $R^1$ and $R^2$ each independently represent an alkoxyalkyl group, or an alkoxyalkylenoxyalkyl group, $R^3$ represents a hydrogen atom, an alkoxy group, an alkenyloxy group, a hydroxy group, an acyl group, an alkyl group, or an alkenyl group, and $R^4$ represents a hydrogen atom, an alkoxy group, an alkenyloxy group, a hydroxy group, an acyl group, an alkyl group, an alkenyl group, or a group $$-CH=C\begin{matrix}COOR^1\\COOR^2\end{matrix},$$

wherein $R^1$ and $R^2$ have the same meaning as defined above.

3. The ultraviolet ray absorber according to claim 2, wherein $R^3$ in formula (4) is a hydrogen atom, an alkoxy group, or a hydroxy group.

4. The ultraviolet ray absorber according to claim 2, wherein $R^3$ in formula (4) is a hydrogen atom, an alkoxy group, or a hydroxy group, and $R^4$ is a hydrogen atom, an alkoxy group, or a group $$-CH=C\begin{matrix}COOR^1\\COOR^2\end{matrix},$$

wherein $R^1$ and $R^2$ have the same meaning as defined above.

5. An ultraviolet ray absorber, comprising a naphthalenemethylenemalonic diester represented by the following formula (5):

$$R^1OCO\\R^2OCO\end{matrix}C=CH-\text{[naphthalene]}-CH=C\begin{matrix}COOR^1\\COOR^2\end{matrix} \quad (5)$$

wherein $R^1$ and $R^2$, each independently represent a hydrocarbon group, an alkoxyalky group, or an alkoxyalkyleneoxyalkyl group.

6. The ultraviolet ray absorber according to claim 2, wherein $R^1$ and $R^2$ in formula (4) are each independently C1–C20 hydrocarbon, (C1–C20)alkoxy-(C1–C20)alkyl, or (C1–C20)alkoxy-(C1–C5)alkylenoxy-(C1–C20)alkyl; $R^3$ in formula (4) is hydrogen, C1–C20 alkoxy, C2–C20 alkenyloxy, hydroxy, C1–C20 acyl, C1–C20 alkyl, or C2–C20 alkenyl; and $R^4$ in formula (4) is hydrogen, or a group $$-CH=C\begin{matrix}COOR^1\\COOR^2\end{matrix},$$

wherein $R^1$ and $R^2$ have the same meaning as defined above.

7. A cosmetic composition comprising 0.1 to 20 wt. % of a naphthalenemethylenemalonic diester represented by the following formula (1):

$$NAP-CH=C\begin{matrix}COOR^1\\COOR^2\end{matrix}$$

wherein NAP represents a naphthalene group which may optionally have a substituent, and $R^1$ and $R^2$ each independently represent a hydrocarbon group, an alkoxyalkyl group, or an alkoxyalkylenoxyalkyl group, and a carrier.

8. The cosmetic composition according to claim 7, comprising a naphthalenemethylenemalonic diester represented by the following formula (4):

$$R^4-\text{[naphthalene with }R^3\text{]}-CH=C\begin{matrix}COOR^1\\COOR^2\end{matrix} \quad (4)$$

wherein $R^1$ and $R^2$ each independently represent a hydrocarbon group, an alkoxyalkyl group, or an alkoxyalkylenoxyalkyl group, $R^3$ represents a hydrogen atom, an alkoxy group, an alkenyloxy group, a hydroxy group, an acyl group, an alkyl group, or an alkenyl group, and $R^4$ represents a hydrogen atom, an alkoxy group, an alkenyloxy group, a hydroxy group, an acyl group, an alkyl group, an alkenyl group, or a group $$-CH=C\begin{matrix}COOR^1\\COOR^2\end{matrix},$$

wherein $R^1$ and $R^2$ have the same meaning as defined above.

9. The cosmetic composition according to claim 8, wherein $R^3$ in formula (4) is a hydrogen atom, an alkoxy group, or a hydroxy group.

10. The cosmetic composition according to claim 8, wherein $R^3$ in formula (4) is a hydrogen atom, an alkoxy group, or a hydroxy group, and $R^4$ is a hydrogen atom, an alkoxy group, or a group

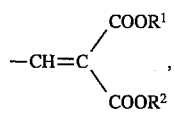

wherein $R^1$ and $R^2$ have the same meaning as defined above.

11. A cosmetic composition, comprising a naphthalenemethylenemalonic diester represented by the following formula (5):

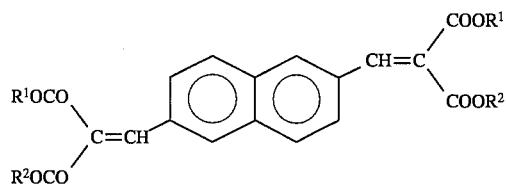 (5)

wherein $R^1$ and $R^2$ independently represent a hydrocarbon group, an alkoxyalkyl group, or an alkoxyalkyleneoxalkyl group.

12. The cosmetic composition according to claim 8, wherein $R^1$ and $R^2$ in formula (4) are each independently C1–C20 hydrocarbon, (C1–C20)alkoxy-(C1–C20)alkyl, or (C1–C20)alkoxy-(C1–C5)alkylenoxy-(C1–C20)alkyl; $R^3$ in formula (4) is hydrogen, C1–C20 alkoxy, C2–C20 alkenyloxy, hydroxy, C1–C20 acyl, C1–C20 alkyl, or C2–C20 alkenyl; and $R^4$ in formula (4) is hydrogen, or a group

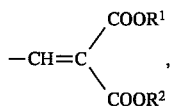

wherein $R^1$ and $R^2$ have the same meaning as defined above.

13. A naphthalenemethylenemalonic diester represented by the following formula (2):

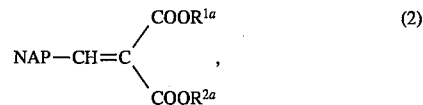 (2)

wherein NAP represents a naphthalene group which may optionally have a substituent, and $R^{1a}$ and $R^{2a}$ each independently represent a C7–C20 hydrocarbon group, a (C1–C12)alkoxy-(C1–C20)alkyl group, or a (C1–C12)alkoxy-(C1–C5)alkylenoxy-(C1–C20)alkyl group.

14. A naphthalenemethylenemalonic diester represented by the following formula (6):

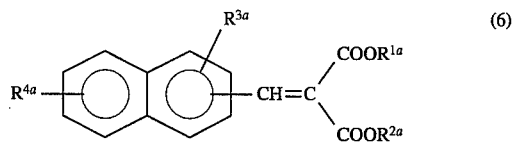 (6)

wherein $R^{3a}$ represents a hydrocarbon atom, a C1–C20 alkoxy group or a hydroxy group, $R^{4a}$ represents a hydrogen atom, a C1–C20 alkoxy group, and $R^{1a}$ and $R^{2a}$ each independently represent a C7–C20 hydrocarbon group, a (C1–C12)alkoxy-(C1–C20)alkyl group, or a (C1–C20)alkoxy-(C1–C5)alkylenoxy-(C1–C20)alkyl group.

15. A naphthalenemethylenemalonic diester represented by the following formula (3):

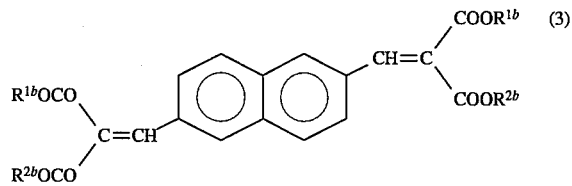 (3)

wherein $R^{1b}$ and $R^{2b}$ each independently represent a C1–C20 hydrocarbon group.

* * * * *

UNITED STATES PATENT AND TRADEMARK OFFICE
CERTIFICATE OF CORRECTION

PATENT NO. : 5,508,025
DATED : April 16, 1996
INVENTOR(S) : Masahide HOSHINO, et al.

It is certified that error appears in the above-indentified patent and that said Letters Patent is hereby corrected as shown below:

Column 6, line 63, after "vatives " delete the semi-colon.

Column 18, line 10, "an alkoxyalky group" should read --alkoxyalkyl group--.

line 14, Delete "C1-C20 hydrocarbon."

line 30, "  " should read

-- 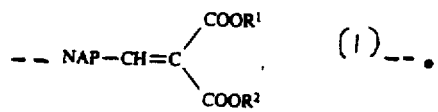  --.

Column 19, line 23, "alkoxyalkyleneoxalkyl" should read --alkoxyalkyleneoxyalkyl--.

Signed and Sealed this

Second Day of December, 1997

Attest:

BRUCE LEHMAN

Attesting Officer

Commissioner of Patents and Trademarks